(12) United States Patent
Anderson et al.

(10) Patent No.: US 8,721,552 B2
(45) Date of Patent: May 13, 2014

(54) COMPRESSIVE SURFACES FOR ULTRASONIC SCANNING

(75) Inventors: Tor C. Anderson, Los Gatos, CA (US);
Jiayu Chen, Palo Alto, CA (US);
Shih-Ping Wang, Los Altos, CA (US)

(73) Assignee: U-Systems, Inc., San Jose, CA (US)

( * ) Notice: Subject to any disclaimer, the term of this patent is extended or adjusted under 35 U.S.C. 154(b) by 0 days.

(21) Appl. No.: 13/489,091

(22) Filed: Jun. 5, 2012

(65) Prior Publication Data

US 2012/0302887 A1 Nov. 29, 2012

Related U.S. Application Data

(63) Continuation of application No. 12/769,440, filed on Apr. 28, 2010, now Pat. No. 8,241,219, which is a continuation of application No. 11/917,466, filed as application No. PCT/US2006/029179 on Jul. 25, 2006, now Pat. No. 7,731,662.

(60) Provisional application No. 60/702,202, filed on Jul. 25, 2005, provisional application No. 60/713,322, filed on Aug. 31, 2005.

(51) Int. Cl.
*A61B 8/00* (2006.01)

(52) U.S. Cl.
USPC .......................................... 600/459; 600/443

(58) Field of Classification Search
None
See application file for complete search history.

(56) References Cited

U.S. PATENT DOCUMENTS

| | | | | |
|---|---|---|---|---|
| 7,556,602 B2 * | 7/2009 | Wang et al. | | 600/437 |
| 7,731,662 B2 * | 6/2010 | Anderson et al. | | 600/459 |
| 8,128,568 B2 * | 3/2012 | Wang et al. | | 600/459 |
| 8,241,219 B2 * | 8/2012 | Anderson et al. | | 600/459 |
| 2003/0007598 A1 | 1/2003 | Wang et al. | | |
| 2004/0015080 A1 | 1/2004 | Kelly et al. | | |
| 2006/0235303 A1 | 10/2006 | Vaezy et al. | | |
| 2007/0055159 A1 | 3/2007 | Wang et al. | | |
| 2008/0269613 A1 * | 10/2008 | Summers et al. | | 600/459 |
| 2009/0024039 A1 | 1/2009 | Wang et al. | | |

FOREIGN PATENT DOCUMENTS

| | | |
|---|---|---|
| JP | 2004305422 | 4/2001 |
| JP | 2004516865 | 6/2004 |
| WO | WO 2007/014292 A2 | 2/2007 |

* cited by examiner

*Primary Examiner* — Unsu Jung
*Assistant Examiner* — Amanda Lauritzen Moher
(74) *Attorney, Agent, or Firm* — Alleman Hall McCoy Russell & Tuttle LLP

(57) ABSTRACT

Automated ultrasonic scanning of a chestwardly compressed breast of a supine patient uses a scanning assembly that moves down to compress the breast through a membrane that is secured to the assembly across a bottom opening. A motorized ultrasound transducer moves across the breast while the breast remains downwardly compressed against the patient's chest, sending and receiving ultrasound energy through the membrane. The membrane is porous with respect to an acoustic coupling liquid that impregnates it. The transducer outputs ultrasound information that is processed to form initial planar images and then reconstructed slice images of breast tissue.

20 Claims, 14 Drawing Sheets

FIG. 9C 902'

COMPRESSIVE SURFACES FOR ULTRASONIC SCANNING

CROSS-REFERENCE TO RELATED APPLICATIONS

This application is a continuation of application Ser. No. 12/769,440 filed Apr. 28, 2010, now U.S. Pat. No. 8,241,219 which in turn is a continuation of application Ser. No. 11/917,466, filed Aug. 22, 2008, now U.S. Pat. No. 7,731,662, as a U.S. national stage application under 35 U.S.C. 371 of International Application No. PCT/US 2006/029179 filed Jul. 25, 2006, which claims the benefit of US. Provisional Application No. 60/702,202, filed Jul. 25, 2005, and US. Provisional Application No. 60/713,322, filed Aug. 31, 2005, the entire contents of each of which are incorporated by reference herein.

FIELD

This provisional patent specification relates to medical imaging. More particularly, this provisional patent specification relates to the facilitation of ultrasonic tissue scanning.

BACKGROUND

Volumetric ultrasound scanning usually involves the movement of an ultrasound transducer relative to a tissue sample and the processing of resultant ultrasound echoes to form a data volume representing at least one acoustic property of the tissue sample. Although several examples herein are presented in the particular context of human breast ultrasound, it is to be appreciated that the present teachings are broadly applicable for facilitating ultrasonic scanning of any externally accessible human or animal body part (e.g., abdomen, legs, feet, arms, neck, etc.). Moreover, although several examples herein are presented in the particular context of mechanized scanning (i.e., in which the ultrasound transducer is moved by a robot arm or other automated or semi-automated mechanism), it is to be appreciated that one or more aspects of the present teachings can be advantageously applied in a handheld scanning context.

Volumetric ultrasound scanning of the breast has been proposed as a complementary modality for breast cancer screening as described, for example, in the commonly assigned US 2003/007598A1 published Jan. 9, 2003, which is incorporated by reference herein. The commonly assigned WO 2004/030523A2 published Apr. 15, 2004, which is incorporated by reference herein, describes a full-field breast ultrasound (FFBU) scanning apparatus that compresses a breast along planes such as the craniocaudal (CC) plane, the mediolateral oblique (MLO) plane, etc., and ultrasonically scans the breast. One side of an at least partially conformable, substantially taut membrane or film sheet compresses the breast. A transducer translation mechanism maintains an ultrasound transducer in contact with the other side of the film sheet while translating the ultrasound transducer thereacross to scan the S breast.

Other FFBU scanning devices that compress the breast in other directions, such as in generally chestward or "head-on" directions, are described in one or more of the following commonly assigned applications, each of which is incorporated by reference herein: U.S. Ser. No. 60/565,698 filed Apr. 26, 2004; U.S. Ser. No. 60/577,078 filed Jun. 4, 2004; U.S. Ser. No. 60/629,007 filed Nov. 17, 2004; WO 2005/104729A2 published Nov. 10, 2005; and WO 2005/120357A1 Published Dec. 22, 2005. It would be desirable to facilitate ultrasound scanning of a tissue volume (such as, but not limited to, a breast) in a manner that further improves image quality. Other issues arise as would be readily apparent to one skilled in the art in view of the present disclosure.

SUMMARY

In one embodiment, an apparatus and related methods for ultrasonically scanning a tissue sample are provided, the apparatus comprising an ultrasound transducer and a taut fabric sheet compressing the tissue sample, the ultrasound transducer contacting the taut fabric sheet and ultrasonically scanning the tissue sample therethrough. Preferably, the taut fabric sheet is substantially porous with respect to an acoustic couplant.

In another embodiment, an apparatus and related methods for ultrasonically scanning a tissue volume having a tissue surface is provided, comprising an ultrasound transducer and a vented membrane. The vented membrane has a first surface contacting the tissue surface and a second surface opposite the first surface. The ultrasound transducer contacts the second surface and is translated across the second surface for ultrasonically scanning the tissue volume. An acoustic couplant is applied to one of the tissue surface, the first surface, and the second surface, the vented membrane being substantially porous with respect to the acoustic coupling agent. The vented membrane has a void pattern providing this porosity.

As used in accordance with one or more of the embodiments, a couplant-porous material sheet, i.e., a couplant-porous fabric sheet or a vented membrane, promotes dissipation of air bubbles that might otherwise form in the acoustic couplant at the compressive surface which, in turn, promotes enhanced image quality, and furthermore promotes locational stability of the tissue surface by virtue of the material textures provided. Other advantages are brought about as would be apparent to one skilled in the art in view of the present disclosure.

BRIEF DESCRIPTION OF THE DRAWINGS

FIG. 8 and FIGS. 9A-9D illustrate some of the many different overall device configurations in which taut fabric sheets according to the present teachings can be used for facilitating ultrasonic breast scanning;

DETAILED DESCRIPTION

Figure 1:
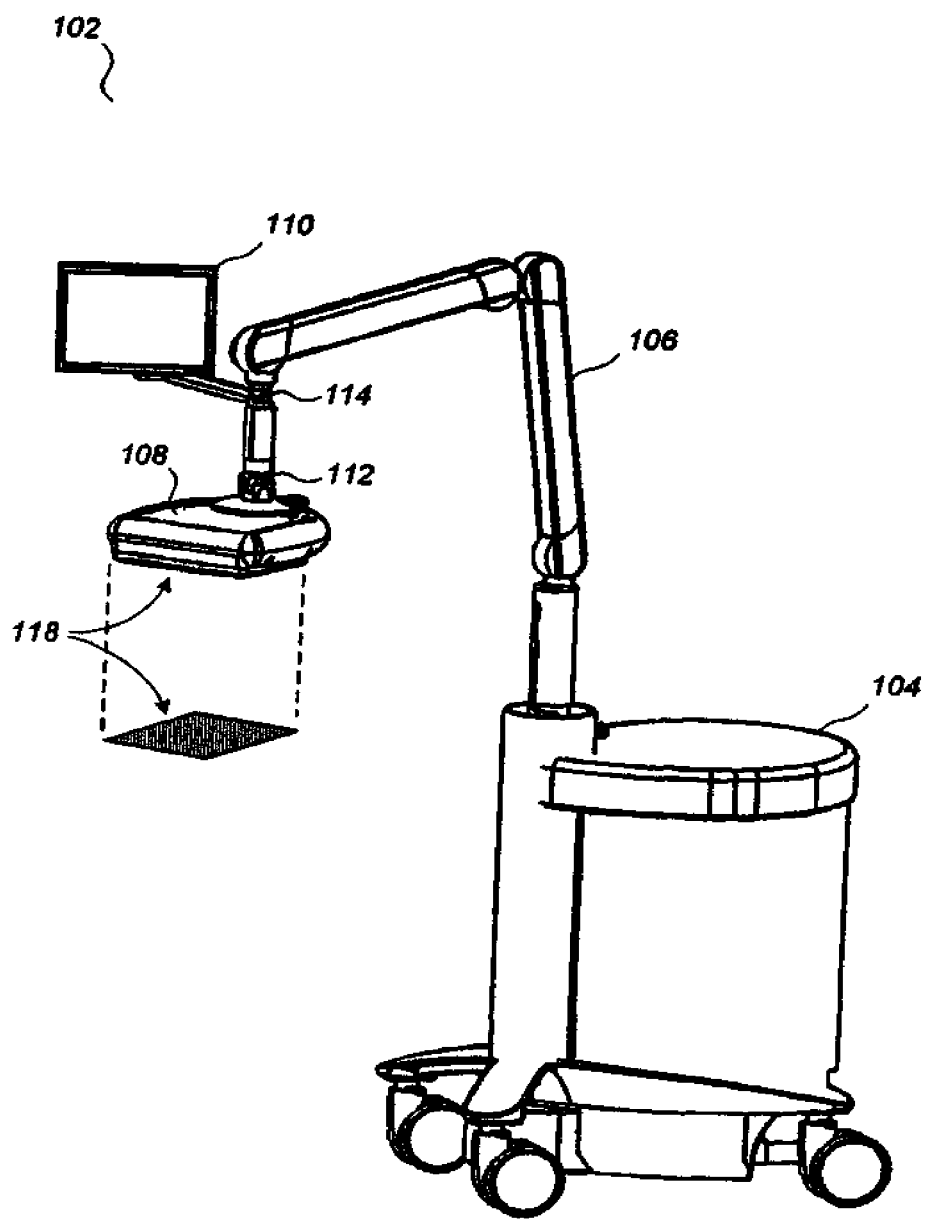
FIG. 1 illustrates a perspective view of a full-field breast ultrasound (FFBU) scanning apparatus according to an embodiment.

In one embodiment, the taut fabric sheet compresses the tissue sample to have a generally planar shape, the ultrasound transducer being translated along a generally planar path while scanning the tissue sample through the taut fabric sheet for volumetric scanning of the compressed tissue sample. For this embodiment, the taut fabric sheet may have a minor degree of outward bulge due to the outward force of the tissue sample. For such embodiment, the ultrasound transducer may be driven along a precisely planar path, thereby locally deforming the taut fabric sheet and the tissue sample by a small amount while passing thereover. Alternatively, the ultrasound transducer can be controlled so as to follow along the outward bulge in a conformal manner while scanning the tissue sample through the taut fabric sheet In another embodiment, the taut fabric sheet compresses the tissue sample to have a desired three-dimensionally shaped surface, the ultrasound transducer being translated to follow along the three-dimensionally shaped surface while scanning the tissue sample through the taut fabric sheet. Preferably, the taut fabric sheet is wetted with an acoustic couplant facilitating acoustic coupling between the ultrasound transducer and the tissue sample. Preferably, the taut fabric sheet is substantially porous with respect to the acoustic couplant to discourage the presence of air bubbles in an acoustic path between the ultrasound transducer and the tissue sample. The taut fabric sheet may be wetted with the acoustic couplant by one or more of: (i) pre-impregnating the taut fabric sheet with the acoustic couplant; (ii) applying the coupling agent to a tissue-facing surface of the taut fabric sheet, or to the tissue surface, prior to compressing the tissue sample; (iii) applying the coupling agent to a transducer-facing surface of the taut fabric sheet prior to compressing the tissue sample; and (iv) applying the coupling agent to a transducer-facing surface of the taut fabric sheet subsequent to compressing the tissue sample and prior to the scanning.

In one embodiment, the taut fabric sheet compresses the breast in a generally head-on direction. In another embodiment, the taut fabric sheet compresses the breast along a standard x-ray mammogram plane (e.g., CC, MLO, LAT, etc.) The taut fabric sheet preferably compresses the breast with a compressive force between about 2-20 lbs. More preferably, the taut fabric sheet compresses the breast with a compressive force of about 4-12 lbs. Even more preferably, the taut fabric sheet compresses the breast with a compressive force of about 6-10 lbs.

As used herein, fabric refers generally to a material structure of interconnected parts, such as can be formed by knitting, weaving, or felting natural or synthetic fibers, assembling natural or synthetic fibers together into an interlocking arrangement, fusing thermoplastic fibers, or bonding natural or synthetic fibers together with a cementing medium, and further refers to materials having similar textures or qualities as those formed thereby, such as animal membranes or other naturally occurring substances having fabric-like properties (either inherently or by processing), and such as materials generated by chemical processes yielding fabric-like webbings.

In one embodiment, the taut fabric sheet is substantially inelastic. Preferably, the taut fabric sheet is sheer to allow viewing of the compressed tissue sample therethrough. One particularly suitable material for the taut fabric sheet comprises a polyester organza material having a filament diameter of about 40 microns and a filament spacing of about 500 microns. However, the taut fabric sheet may comprise any of a variety of other fabrics that are substantially inelastic and generally porous to ultrasound couplants without departing from the scope of the present teachings. Examples include, but are not limited to, polyester chiffon fabrics and cloth fabrics comprising straight weaves of substantially inelastic fibers. Where the weave is particularly tight (for example, the cloth used in men's dress shirts or the cloth used in many bed sheets), porosity can be achieved by perforating the cloth or otherwise introducing irregularities that allow the ultrasound couplant to soak or seep through.

FIG. 1 illustrates a perspective view of a full-field breast ultrasound (FFBU) scanning apparatus 102 according to an embodiment, comprising a frame 104 that may contain an ultrasound processor, a movable support arm 106, a compression/scanning assembly 108 connected to the support arm 106 via a ball-and-socket connector 112, and a monitor 110 connected to the support arm 106 at a joint 114. Preferably, the support arm 106 is configured and adapted such that the compression/scanning assembly 108 is either (i) neutrally buoyant in space, or (ii) has a light net downward weight (e.g., 2-3 pounds) for breast compression, while allowing for easy user manipulation.

Compression/scanning assembly 108 comprises a taut fabric sheet 118 for compressing a breast, the taut fabric sheet 118 having a bottom surface contacting the breast while a transducer is swept across a top surface thereof to scan the breast. Optionally, the support arm 106 may comprise potentiometers (not shown) to allow position and orientation sensing for the compression/scanning assembly 108, or other types of position and orientation sensing (e.g., gyroscopic, magnetic, optical, radio frequency (RF)) can be used. Within frame 104 may be provided a fully functional ultrasound engine for driving an ultrasound transducer and generating volumetric breast ultrasound data from the scans in conjunction with the associated position and orientation information. The volumetric scan data can be transferred to another computer system for further processing using any of a variety of data transfer methods known in the art. A general purpose computer, which can be implemented on the same computer as the ultrasound engine, is also provided for general user interfacing and system control. The general purpose computer can be a self-contained stand-alone unit, or can be remotely controlled, configured, and/or monitored by a remote station connected across a network.

Figure 2:
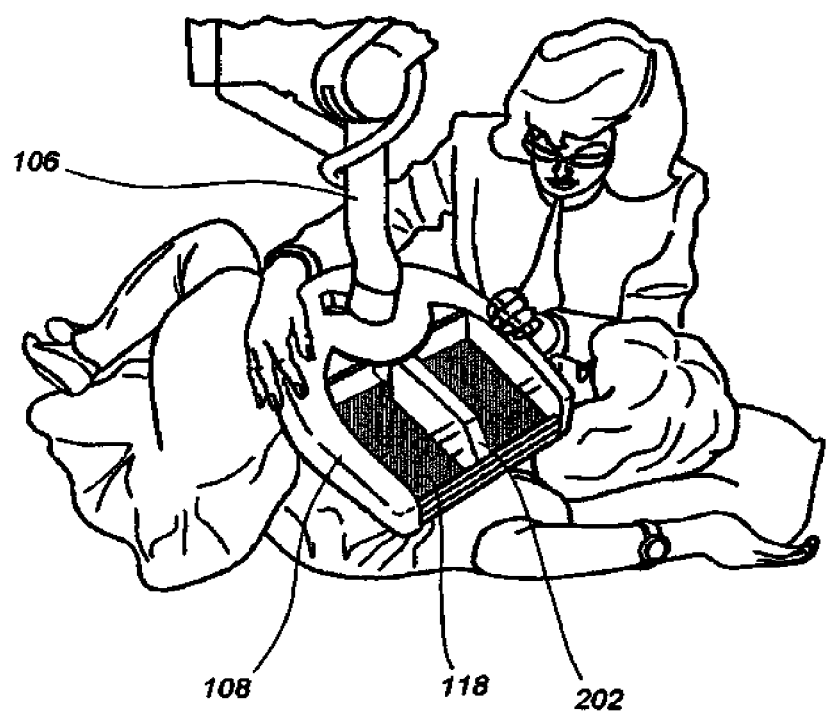
FIG. 2 illustrates a perspective view of ultrasonic breast scanning using the FFBU of FIG. 1 according to an embodiment.

FIG. 2 illustrates one example of how the compression/scanning assembly 108 including the taut fabric sheet 118 may be used for ultrasonic breast scanning. An ultrasound transducer 202 housed within the compression/scanning assembly 108 is swept across the breast as illustrated. Preferably, the taut fabric sheet 118 is wetted with an acoustic couplant facilitating acoustic coupling between the ultrasound transducer and the tissue sample. Preferably, the taut fabric sheet 118 is substantially porous with respect to the acoustic couplant to discourage the presence of air bubbles in an acoustic path between the ultrasound transducer and the tissue sample.

In one embodiment, the fabric sheet is pre-impregnated with the acoustic couplant. In another embodiment, the fabric sheet is not pre-impregnated with the acoustic couplant. Using a non-pre-impregnated (i.e., dry) fabric sheet is advantageous in that it is easier for the technician to see the breast therethrough during breast positioning as compared to using a pre-impregnated fabric sheet. For embodiments in which a chiffon or organza fabric is used, it has been found that applying the acoustic couplant directly to the breast, and then bringing the fabric sheet into taut, compressible contact with the couplant-coated breast, yields particularly good image quality.

In one embodiment, the fabric sheet is a permanent or semi-permanent component of the FFBU scanner, and is sterilized after each patient. In another embodiment, the fabric sheet is disposable or recyclable, and is replaced after each patient. By way of example, the fabric sheet can be rolled up onto a long roll that is attached to the frame of the compressive member, and that roll can be progressively advanced between patients such that each patient uses a fresh piece of the fabric sheet. Assemblies can be provided as needed to tension, release, and re-tension the fabric sheet.

Several advantages are realized by using a taut fabric sheet that is substantially porous to acoustic couplant liquid according to the present teachings. First, the taut fabric sheet promotes dissipation of air bubbles that might otherwise form in the acoustic couplant at the membrane surface. As compared to using a material nonporous to the acoustic couplant, image quality is increased by virtue of fewer air bubbles being present between the ultrasound transducer and the tissue surface. Second, the surface textures of the taut fabric sheet promote locational stability of the tissue surface, the skin being at least partially "grabbed" by the textures. The breast is thereby inhibited from slipping or sliding along the compressive surface. This makes patient and breast positioning easier, and also reduces the possibility that the breast may slip while the transducer is being translated. Third, the flattening or compression of the breast, which is achieved using the taut fabric sheet, in turn provides for thorough volumetric imaging and/or standardized volumetric imaging as described in US 2003/007598A1 and WO 2004/030523A2, supra. The scanned breast volume may, if desired, be easily visualized by viewing an array of thick-slice images of slab-like subvolumes generally parallel to the plane of compression. Other advantages are brought about as would be apparent to one skilled in the art in view of the present disclosure. For example, in embodiments for which the taut fabric sheet is sheer (i.e., thin, fine, and relatively transparent), easier viewing of the breast is provided therethrough (as compared to using a relatively opaque fabric), which further facilitates patient positioning and monitoring of the progress and/or quality of the scanning process.

Figure 3:
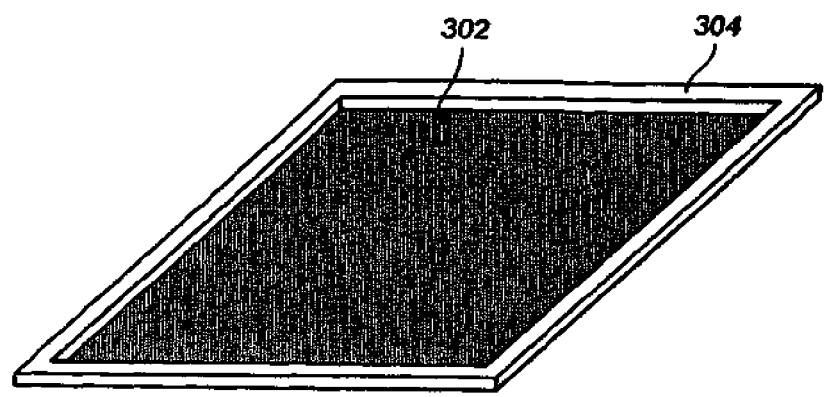
FIG. 3 illustrates a taut fabric sheet according to an embodiment.

FIG. 3 illustrates a taut fabric sheet 302 according to an embodiment, the taut fabric sheet 302 being attached to a frame 304. In this embodiment, the fabric material is already provided in a taut state as tensionably mounted to the frame 304. This can be contrasted with at least one other embodiment Infra in which the fabric material is provided in a relaxed state, and becomes taut as the breast is compressed.

Figure 4:
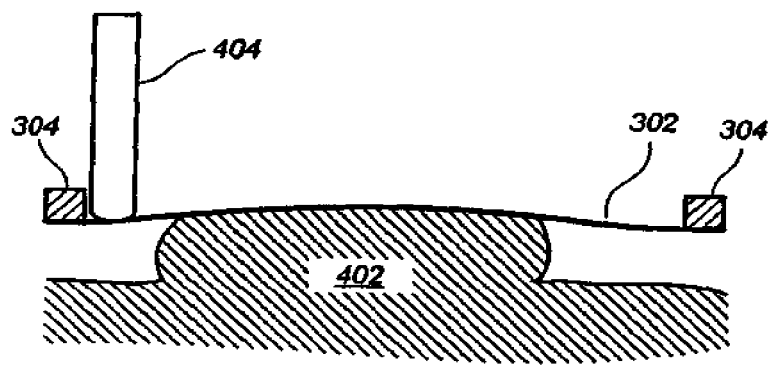
FIG. 4 and FIGS. 5A-5B illustrate a side view of ultrasonic breast scanning using the taut fabric sheet of FIG. 3.

FIG. 4 illustrates the taut fabric sheet 302 compressing a breast 402 according to an embodiment. Although generally planar, the taut fabric sheet 302 exhibits some degree of outward bulging or bowing due to the upward force of the breast 402 thereagainst. An ultrasound transducer 404 is poised to scan the breast 402 by being swept over the taut fabric sheet 302 in contact therewith.

Figure 5A:
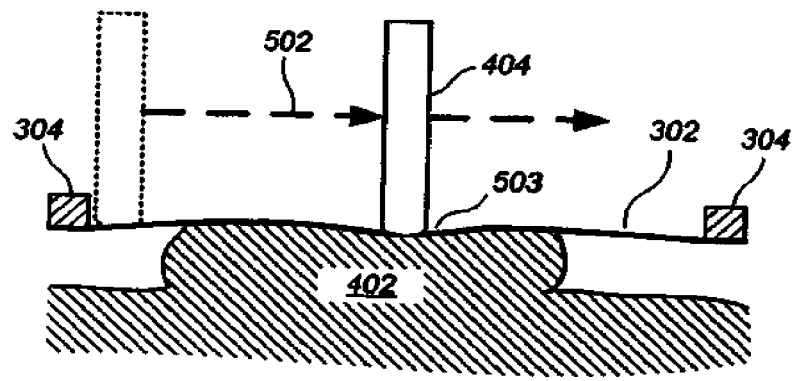
Figure 5B:
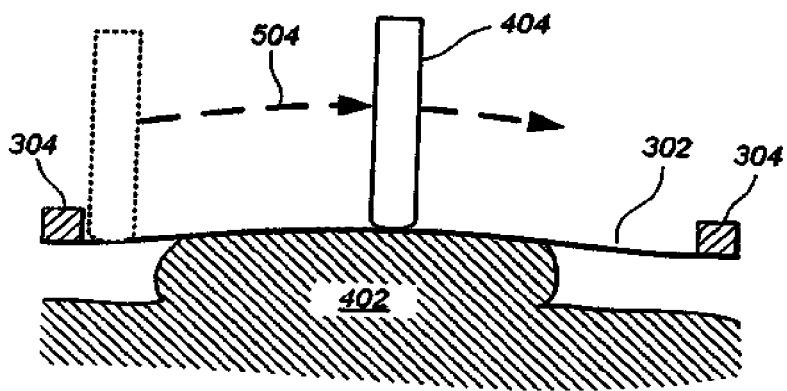

FIG. 5A illustrates the taut fabric sheet 302 and ultrasound transducer 404 according to one embodiment, wherein the ultrasound transducer 404 is maintained strictly on a planar path 502 during the scanning process despite the outward bulging of the taut fabric sheet 302. In this embodiment, there is a local deformity 503, usually small, around the current position of the ultrasound transducer 404. FIG. 58 illustrates the taut fabric sheet 302 and ultrasound transducer 404 according to another embodiment, wherein the ultrasound transducer 404 is mechanically controlled so as to follow 504 along the outward bulge in a conformal manner while scanning the breast 402 through the taut fabric sheet 302.

Figure 6A:
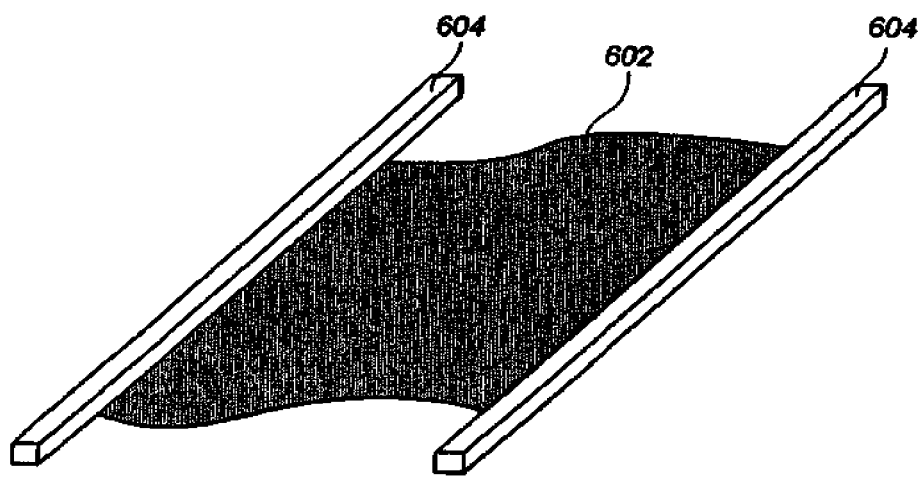
FIG. 6A illustrates a fabric sheet in a generally relaxed (non-taut) state.

FIG. 6A illustrates a fabric sheet 602 as provided for use in an ultrasound scanning apparatus according to an embodiment, wherein the fabric sheet is provided in a generally relaxed (non-taut) state. Frame elements 604 are provided on each side of the fabric sheet 602. In other embodiments, the frame elements 604 can be replaced by roller elements that feed and receive new fabric, or by a variety of other framing configurations. In still other embodiments, the frame elements 604 can form a single frame similar to the frame 304 of FIG. 3. In each case according to the embodiment of FIGS. 6A-6B, the fabric sheet is initially in a relaxed/limp/non-taut state, and then the frame elements are manipulated relative to the breast 402 such that the fabric sheet 602 is placed into a taut state that compresses the breast 402, as illustrated in FIG. 6B.

Figure 6B:
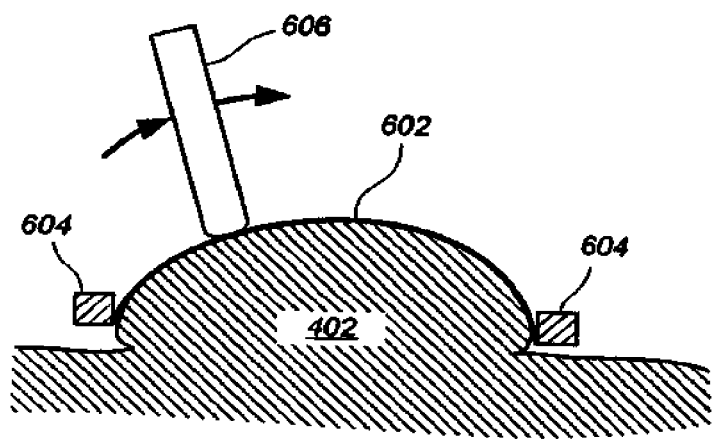
FIG. 6B illustrates the fabric sheet of FIG. 6A in a taut state while underlying tissue is being scanned therethrough in accordance with an embodiment.

In the example of FIG. 6B, the taut fabric sheet 602 compresses the tissue sample into a shape resembling a longitudinally-extending sector of a cylinder. More generally, the breast may be compressed to have a desired three-dimensionally shaped surface (e.g., spheroidal, ellipsoidal, etc.). As illustrated in FIG. 6B, an ultrasound transducer 604 may be translated to conformally follow along the three-dimensionally shaped surface while scanning the tissue sample through the taut fabric sheet. As with other embodiments, the embodiments of FIGS. 6A-6B are not limited to scenarios in which the tissue sample is a breast. For example, embodiments similar to FIGS. 6A-6B may be suitable and/or adaptable for compressive ultrasonic imaging of the arm, the leg, the neck, the abdomen, or other body part.

Figure 7:
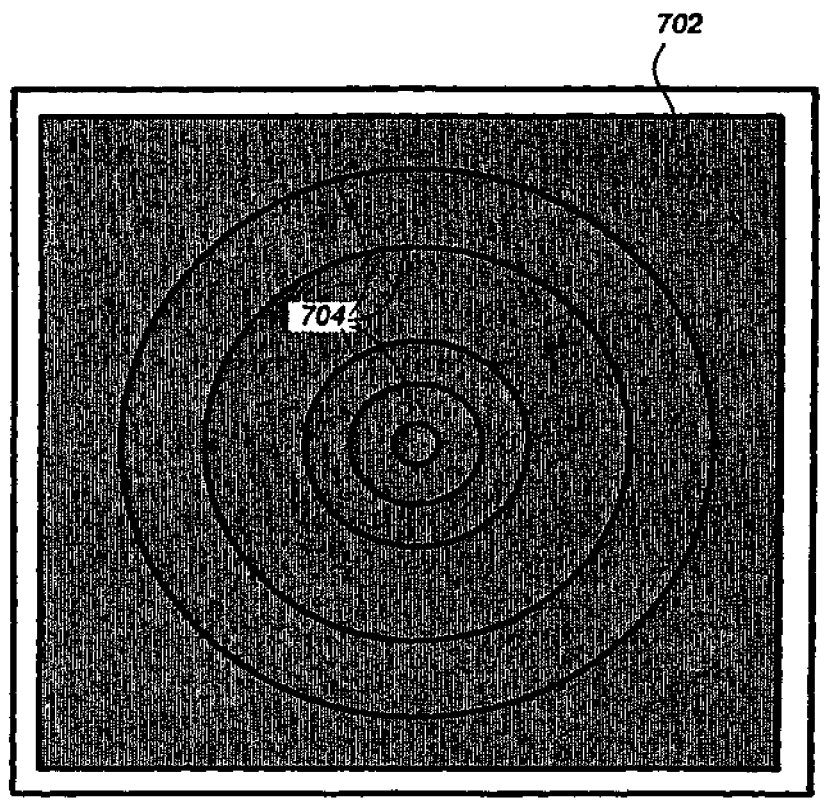
FIG. 7 illustrates a taut fabric sheet having one or more visible markings according to an embodiment.
Figure 8:
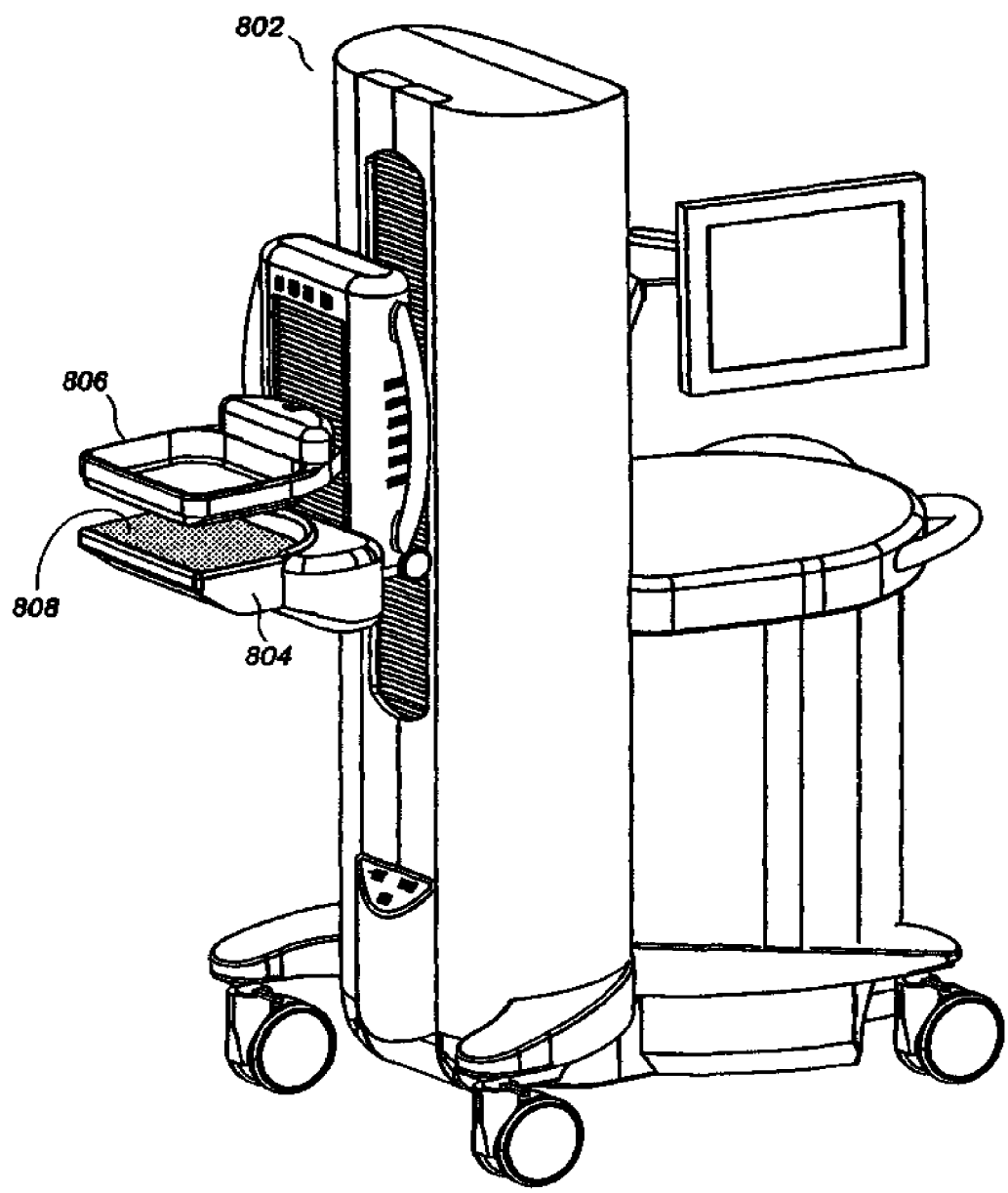

FIG. 7 illustrates a taut fabric sheet 702 according to an embodiment, wherein one or more visible markings 704 are provided for facilitating positioning of the taut fabric sheet 702 relative to the tissue surface. In the embodiment of FIG. 7, the visible demarcations are used to show where the nipple of a breast should be placed. In other embodiments, the visible demarcations can be used to show other useful information such as the scan center, scan borders, preferred orientations, preferred locations for palpable lesions, etc., and/or for providing instructional notations, arrows, text, and the like.

Figure 9A:
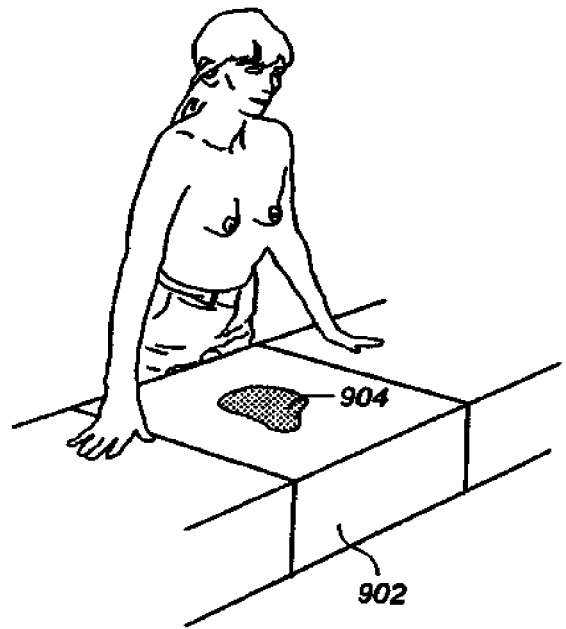
Figure 9B:
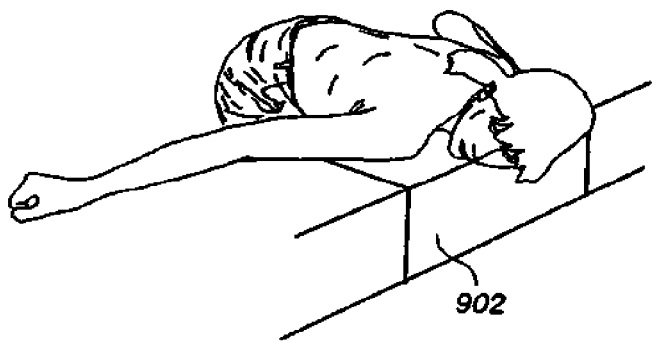
Figure 9D:
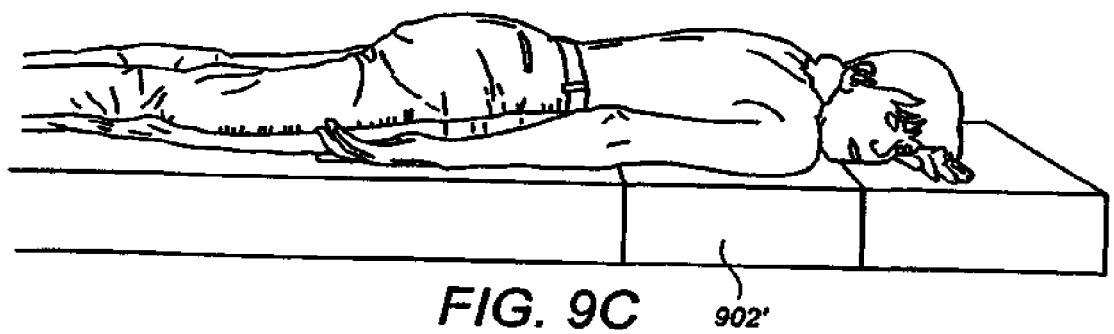
Figure 9D:
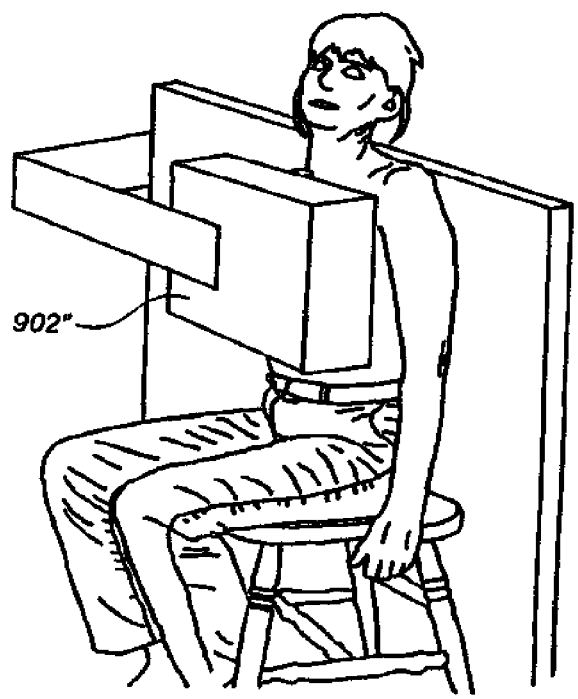

FIG. 8 and FIGS. 9A-9D illustrate some of the many different configurations in which taut fabric sheets according to the present teachings can be used for facilitating ultrasonic breast scanning. FIG. illustrates an FFBU scanner 802 that is particularly adapted for obtaining ultrasound scans while the breast is compressed along mammogram-like view planes such as the CC and MLO views, comprising a compression/scanning assembly 804 and a compressor 806 that can be collectively rotated among CC, MLO, and LAT orientations. The compression/scanning assembly 804 comprises a taut fabric sheet 808 similar to those described supra and yielding similar advantages. In the particular orientation of FIG. 8, the CC compression view is obtained by scanning in an upward direction through the taut fabric sheet 808. FIGS. 9A-9D illustrate how a taut fabric sheet 904 may be advantageously used as part of a leaning-forward prone scanning device 902 (FIGS. 9A-9B), a lying-down prone scanning device 902' (FIG. 9C), and an upright scanning device 902" (FIG. 9D).

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, it is to be appreciated that any of a variety of different frame assemblies can be used that position, tension, and otherwise manipulate the fabric sheet, whether the fabric sheet is permanently used and re-used for different patients or is disposable for each patient, without departing from the scope of the present teachings.

By way of further example, for certain alternative embodiments in which the fabric sheet is a woven material, the weave may optionally comprise different materials woven in different directions (for example, a inelastic polyester fiber in one direction and a partially elastic fiber in another direction) such that the amount of tautness is directionally dependent. Therefore, reference to the details of the embodiments are not intended to limit their scope.

Also provided as an alternative to, or for use in conjunction with, the taut fabric sheet based system described above is an apparatus and related methods for ultrasonically scanning a tissue volume having a tissue surface, comprising an ultrasound transducer and a vented membrane. The vented membrane has a first surface contacting the tissue surface and a second surface opposite the first surface. The ultrasound transducer contacts the second surface and is translated across the second surface for ultrasonically scanning the tissue volume. An acoustic couplant is applied to one of the tissue surface, the first surface, and the second surface, the vented membrane being substantially porous with respect to the acoustic coupling agent for discouraging the presence of air bubbles in an acoustic path between the ultrasound transducer and the tissue surface during the ultrasound scan. The vented membrane has a void pattern providing this porosity. Preferably, the void pattern is configured such that the vented membrane locationally stabilizes the tissue surface against movement during tissue positioning and transducer translation.

In one embodiment the void pattern is spatially uniform. In another embodiment, the void pattern is spatially varying and defines one or more visible markings for facilitating positioning of the vented membrane relative to the tissue surface. Preferably, the size of the voids (and the void pitch) is equal to or greater than the wavelength of the acoustic signals being applied. By way of example, for a 7 MHz ultrasound frequency, the size of the voids should be about 0.5 mm or greater.

In one embodiment, the vented membrane is formed by (a) forming a uniform film sheet, and (b) establishing a void pattern into the uniform film sheet by one of stamping, perforating, or other process designed to establish a void pattern. Examples include laser perforation, perforation using hot needles, die cutting, cold stamping, and hot-stamping.

In one embodiment, the vented membrane is substantially taut and compresses the tissue surface toward a flattened state, the ultrasound transducer being mechanically translated within a single plane. In another embodiment, the vented membrane is flexible and configured to substantially conform upon or around the tissue surface, the ultrasound transducer being translated across the second surface in a manner that follows a contour thereof when so conforming upon or around the tissue surface. By way of non-limiting example, if the tissue volume is a human breast, the vented membrane may conform in a bra-like fashion around the breast contours.

With reference again to FIG. 1 and FIG. 2, supra, the element 118 can alternatively comprise an at least partially conformable vented membrane in a substantially taut state, the vented membrane having a bottom surface contacting the breast while a transducer is swept across a top surface thereof to scan the breast. With reference again to FIG. 8 and FIGS. 9A-9D, supra, the elements 808 and 904 can alternatively comprise an at least partially conformable vented membrane in a substantially taut state, the vented membrane having a bottom surface contacting the breast while a transducer is swept across a top surface thereof to scan the breast.

Several advantages are realized by using a vented membrane according to the present teachings. First, the vented membrane promotes dissipation of air bubbles that might otherwise form in the acoustic couplant at the membrane surface. As compared to using a non-vented membrane, image quality is increased by virtue of fewer air bubbles being present between the ultrasound transducer and the tissue surface. Second, as compared to using a non-vented membrane, there is reduced attenuation (and reduced reflections) by virtue of the fact that there is less membrane material between the ultrasound transducer and the tissue surface. Third, the presence of the void patterns in the vented membrane promotes locational stability of the tissue surface, the skin being "grabbed" by textures formed by the voids. The breast is thereby inhibited from slipping or sliding along the compressive surface. This makes patient and breast positioning easier, and also reduces the possibility that the breast may slip while the transducer is being translated. Other advantages are brought about as would be apparent to one skilled in the art in view of the present disclosure.

Examples of materials that can be used for the vented membrane include, but are not limited to, polypropylene, polyester (including but not limited to Mylar), polyethylene, PTFE, PET, paper, Kevlar, metal, and epoxy-fiber composite materials. In one embodiment, the vented membrane is a permanent or semi-permanent component of the FFBU scanner, and is cleaned after each patient. In another embodiment, the vented membrane is disposable or recyclable, and is replaced after each patient. By way of example, where the vented membrane comprises a Mylar film sheet or similarly flexible and thin material, the vented membrane material can be rolled up onto a long roll that is attached to the frame of the compressive member, and that roll can be progressively advanced between patients such that each patient uses a fresh piece of the vented membrane material. Assemblies can be provided as needed to tension, release, and re-tension the vented membrane material.

Figure 10:
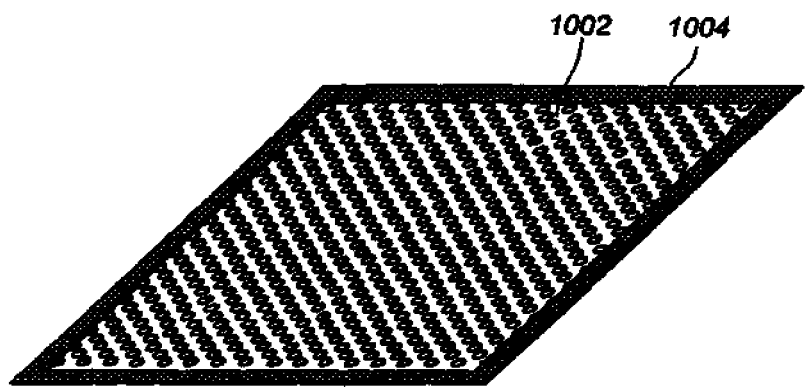
FIGS. 10-13 illustrate one or more vented membranes according to one or more of the embodiments.

FIG. 10 illustrates a vented membrane 1002 according to an embodiment, the vented membrane 1002 being attached to a frame 1004. The vented membrane 1002 may comprise a film sheet less than 1 mm thick, with at least 25% of a surface area of the film sheet being occupied by voids. In another embodiment, at least 80% of the surface area is occupied by voids. In one embodiment, the voids are circular with a uniform diameter between about 0.1 mm 25 mm and have a uniform pitch between about 1.1-10.0 times the diameter. The voids may be arranged in regular lattice patterns (e.g., with unit cells being triangular, square, rectangular, pentagonal, hexagonal, etc) or, alternatively, in any of a variety of randomized arrangements. The randomness may be in terms of void size, void shape, and/or void patterns and may serve to reduce artifacts that might arise at some acoustic frequencies due to short-term or long-term lateral orderings in the vented membrane. More generally, a wide variety of different void shapes, patterns, and dimensions are within the scope of the present teachings.

Figure 11:
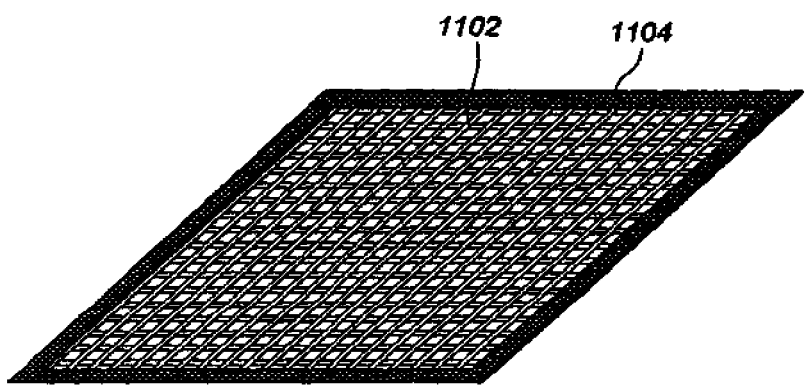
Figure 12:
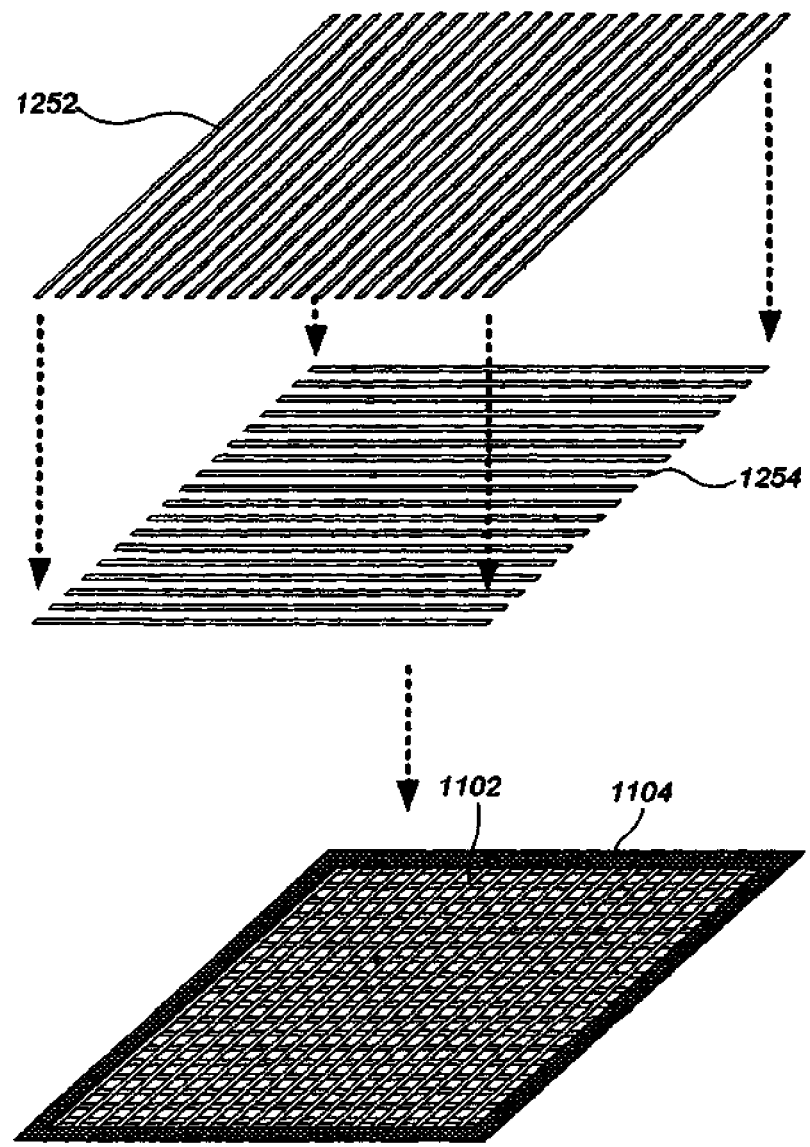

FIG. 11 illustrates a vented membrane 1102 according to an embodiment, the vented membrane 1102 being attached to a frame 1104. Referring Anther to FIG. 12, the vented membrane 1102 comprises a netting formed by a vertical fusing of a first monofilamental pattern 1252 and a second monofilamental pattern 1254. Preferably, at least 25% of a surface area of the netting is occupied by voids. In another embodiment, at least 80% of the surface area is occupied by voids. In still another embodiment, the thickness of the monolilaments is about 0.04 mm at while the pitch is about 0.5 mm, providing for more than 90% of the area being transmissive (i.e., occupied by voids rather than material).

Figure 13:
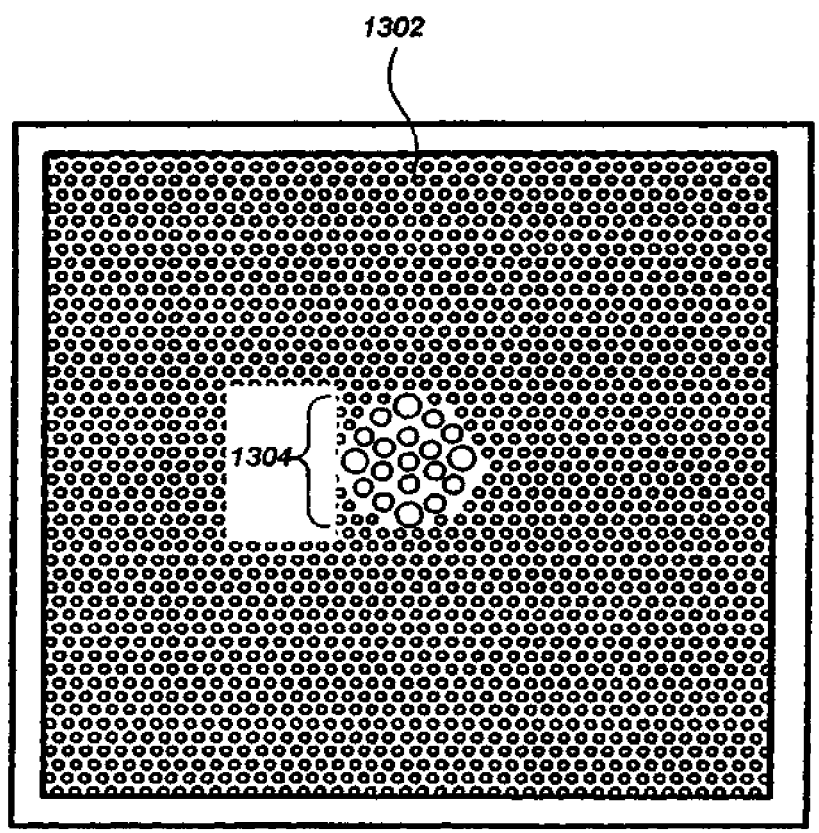

FIG. 13 illustrates a vented membrane 1302 according to an embodiment, wherein the void pattern is spatially varying and defines one or more visible markings for facilitating positioning of the vented membrane relative to the tissue surface. Visible in the embodiment of FIG. 13 is a central area 1304 defined by differently-sized and/or differently positioned voids that can be used to show where the nipple of the breast should be placed.

Figure 14A:
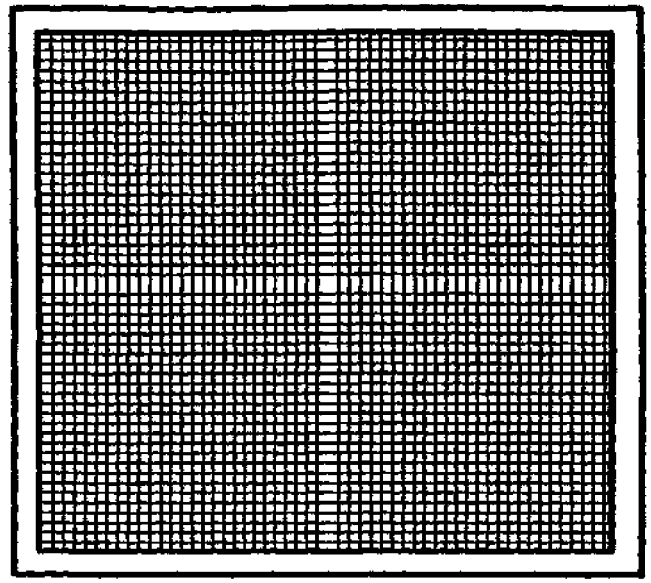
FIGS. 14A-14B illustrate one or more vented membranes according to one or more of the embodiments.
Figure 14B:
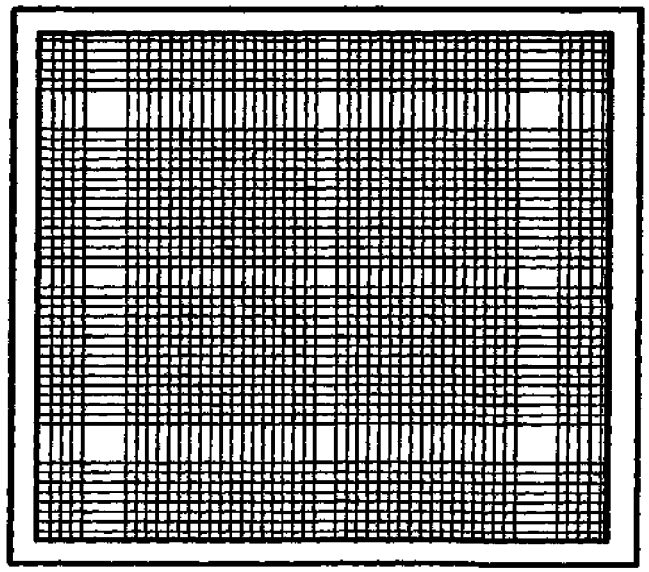

FIGS. 14A and 14B illustrate vented membranes according to an embodiment, wherein the void pattern is spatially varying and defines one or more visible markings for facilitating positioning of the vented membrane relative to the tissue surface. Visible in the embodiment of FIGS. 14A and 14B are variations in the spacings of the monofilamental elements to visibly delineate the center of a scan area. The visible demarcation can be used to show where the nipple of the breast should be placed, and/or where a palpable lesion can be placed. More generally, visible demarcations by variations in the void patterns according to FIGS. 13, 14A, and 14B can take on any of a variety of shapes, forms, and locations for any of a variety of purposes. Thus, for example, FIG. 14B illustrates additional variations in the monofilamental element spacings to demark the edge of the scan area.

In other embodiments, the vented membrane can have varying colors (e.g., printing on the film sheet in FIG. 10, or using differently colored monofilamental elements in FIG. 11) to denote special locations such as the scan center, scan borders, preferred orientations, preferred locations for palpable lesions, etc., and/or for providing instructional notations, arrows, text, and the like. In still other embodiments, combinations of void pattern alterations and printing/coloring can be used to provide such positioning references, notations, etc.

In one embodiment, the vented membrane can be pre-impregnated with the acoustic couplant. In another embodiment, the vented membrane is not pre-impregnated with the acoustic couplant. Using a non-pre-impregnated (i.e., dry) vented membrane is advantageous in that it is easier for the technician to see the breast therethrough during breast positioning as compared to using a pre-impregnated vented membrane. It has been found that applying the acoustic couplant directly to the breast, and then bringing the vented membrane into contact with the couplant-coated breast, yields particularly good image quality. Generally speaking, more acoustic couplant is needed as compared to the amount required with the use of a non-vented membrane.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, it is to be appreciated that any of a variety of different frame assemblies can be used that position, tension, and otherwise manipulate the vented membrane, whether the vented membrane is permanently used and re-used for different patients or is disposable for each patient, without departing from the scope of the present teachings.

By way of further example, while one or more of the embodiments supra is described in terms of a relatively large amount of compressive force being applied by the vented membrane (e.g., to flatten the breast in an x-ray mammogram-like fashion), in other embodiments the compressive force can be very light. For example, in an alternative embodiment, the vented membrane is configured and formed to be worn by the patient in a bra-like fashion, and the ultrasound transducer is moved by a sensitive robotic arm that follows the contours of the breast as maintained inside the bra-like device. In such cases, the compressive forces exerted by the vented membrane can be very light, even approaching zero in some locations, being sufficient only to maintain contact with the skin at those locations. In one alternative embodiment, the vented membrane can comprise material similar to the porous gel bladder materials) discussed in U.S. Pat. No. 5,626,554. Therefore, reference to the details of the embodiments are not intended to limit their scope.

Figure 15A:
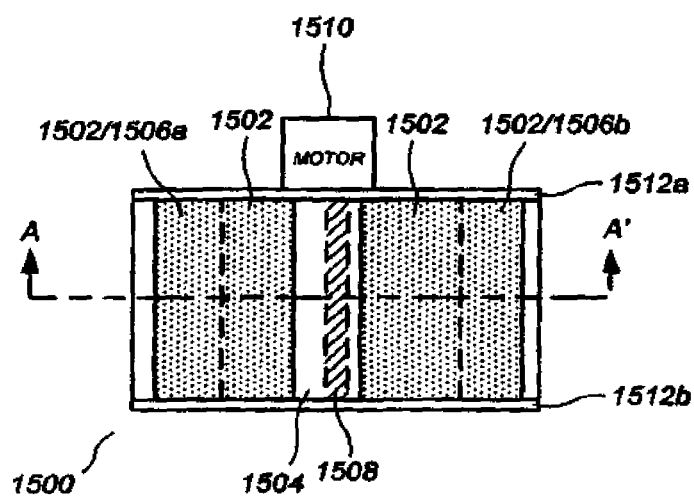
FIGS. 15A-15B illustrate a top view and a side cut-away view, respectively, of a volumetric scanning probe according to an embodiment.
Figure 15B:
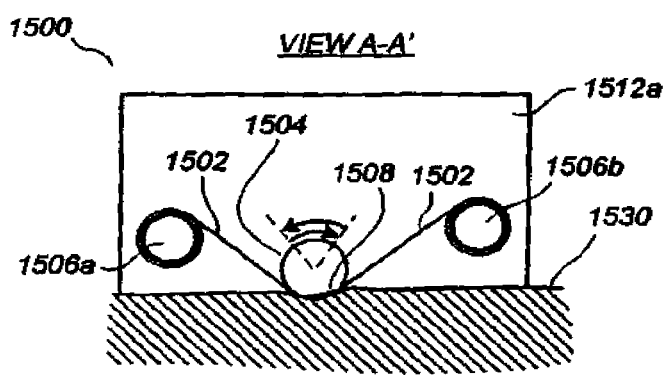

FIGS. 15A-15B illustrate a top view and a side cut-away view, respectively, of a volumetric scanning probe 1500 according to an embodiment in which a flexible couplant-porous material sheet 1502, i.e., a flexible couplant-porous fabric sheet or a flexible vented membrane, is used as a compressive surface between an angularly rotating transducer head 1508 and a tissue surface 1530. The transducer head 1508 is mounted at the periphery of a cylindrical roller 1504 driven by a motor/actuator 1510 in a manner that angularly sweeps the cylindrical roller 1504 back and forth between about −45 degrees and +45 relative to a normal to the tissue surface, the back and forth motion being at a frequency in a range of 0.25 Hz-4 Hz. Turnable members 1506a and 1506b keep the sheet 1502 in a substantially taut state. Optionally, the turnable members 1506a and 1506b can be rollers that store a substantial amount of sheet material 1502, and can progressively renew the sheet material during a scan, and/or renew the sheet material on a per-patient basis for sanitation purposes.

Advantageously, the volumetric scanning probe 1500 can provide for instantaneous or near-instantaneous volumetric images in the tissue near transducer head 1508. Precision is facilitated by the material sheet 1502, which provides for good acoustic coupling using an acoustic wetting agent while also keeping the tissue locationally stable underneath the roller 1504/transducer head 1508. For one embodiment, when the volumetric scanning probe 1500 is laterally translated across the tissue surface, the turnable members 1506a and 1506b are turned by additional actuators (not shown) to feed just the right amount of sheet material 1502 such that there is no sliding of the sheet material 1502 relative to the tissue surface. This is achieved by causing the material sheet to be fed out (in mm/second) at the same speed that the volumetric scanning probe 1500 is being laterally translated across the tissue surface.

Whereas many alterations and modifications of the present invention will no doubt become apparent to a person of ordinary skill in the art after having read the foregoing description, it is to be understood that the particular embodiments shown and described by way of illustration are in no way intended to be considered limiting. Therefore, reference to the details of the embodiments are not intended to limit their scope.

What is claimed is:

1. A device for compressing a patient's breast for scanning the breast with a motorized ultrasound transducer, comprising:
   a compression/scanning assembly including a frame and a breast compression sheet secured thereto, said sheet being made of an acoustically transparent and acoustic couplant permeable porous material, and said frame being configured for releasable attachment to an ultrasound imaging system, the compression/scanning assembly adapted to compress the patient's breast chestwardly and scan the breast through said sheet with the motorized ultrasound transducer moving across the breast;

said sheet being taut at least in one direction when at rest but being partially conformable to locally deform when pressed against the patient's breast while the breast is being scanned therethrough with said motorized ultrasound transducer and said sheet is impregnated with an acoustic couplant; and said porous material being sufficiently sheer to view the compressed breast therethrough at least before said porous material is impregnated with said acoustic couplant;

said porous material including a spatially-varying pore pattern that, when impregnated with said acoustic couplant during said scanning, promotes dissipation of air bubbles that might otherwise form between the breast and said scanning motorized ultrasound transducer, promoting locational stability of breast tissue being scanned, and flattening the breast when pressed against the breast with a selected force.

2. The device of claim 1 in which said breast compression sheet is planar when at rest.

3. The device of claim 1 in which said porous material comprises a woven fabric.

4. The device of claim 3 in which the woven fabric is configured to bow outwardly when pressed against the patient's breast.

5. The device of claim 3 in which the woven fabric comprises polyester filaments.

6. The device of claim 3 in which the woven fabric comprises one or more of polyester chiffon and polyester organza.

7. The device of claim 3 in which the woven fabric comprises filaments that have a filament diameter of 40 microns.

8. The device of claim 3 in which the woven fabric comprises filaments that have a filament spacing of 500 microns.

9. The device of claim 3 in which the woven fabric is taut in all directions when at rest on the frame.

10. The device of claim 3 further including an arm supporting said frame and adapted to bring the woven fabric in pressing chestward contact with the patient's breast and compress the breast with a force in the range of 2-20 lb in a chestward direction.

11. The device of claim 10 in which said force is in the range of 4-12 lb.

12. The device of claim 10 in which said force is in the range of 6-10 lb.

13. The device of claim 1 further including:

a computer system for receiving ultrasound information from said ultrasound transducer while scanning the patient's breast through said sheet while the sheet is impregnated with said acoustic couplant, said computer system being configured to computer-process the ultrasound information to generate initial ultrasound breast images conforming to initial planes and further ultrasound images of the breast that conform to planes transverse to the initial planes; and a computer display for selectively displaying said ultrasound breast images.

14. The device of claim 13 in which said computer system is further configured to selectively combine multiples of said images into a single display image that represents acoustic properties of a slab of breast tissue that is thicker than slices of breast tissue represented by the images that were combined.

15. A method of scanning a patient's breast with ultrasound comprising:

releasably attaching, to an ultrasound breast scanning system, a compression/scanning assembly including a frame and a breast compression sheet secured thereto, said sheet being made of an acoustically transparent and acoustic couplant permeable porous material having a surface area, at least 25% of said surface area being occupied by voids, and said frame compressing a patient's breast chestwardly while a motorized ultrasound transducer in said compression/scanning assembly is scanning the breast through said sheet;

said sheet being taut at least in one direction when at rest but being partially conformable to locally deform when pressed against the patient's breast while the breast is being scanned therethrough with said motorized ultrasound transducer and the sheet is impregnated with an acoustic couplant;

said porous material being sufficiently sheer to view the compressed breast therethrough at least before said porous material is impregnated with said acoustic couplant; and said porous material, when impregnated with said acoustic couplant during said scanning, promoting dissipation of air bubbles that might otherwise form between the breast and the scanning motorized ultrasound transducer, promoting locational stability of breast tissue being scanned, and flattening the breast when pressed against the breast with a selected force.

16. The method of claim 15 in which the sheet is not impregnated with said acoustic couplant before contact with the patient's breast but is impregnated, upon being pressed against the breast, with the acoustic couplant that is on the breast.

17. The method of claim 15 including compressing the breast with said compression sheet using a compression force in the range of 2-20 lb.

18. The method of claim 15 including compressing the breast with said compression sheet using a compression force in the range of 4-12 lb.

19. The method of claim 15 including compressing the breast with said compression sheet using a compression force in the range of 6-10 lb.

20. A device for compressing a patient's breast for scanning the breast with a motorized ultrasound transducer, comprising:

a compression/scanning assembly including a frame and a breast compression sheet secured thereto, said sheet being made of an acoustically transparent and acoustic couplant permeable porous material, and said frame being configured for releasable attachment to an ultrasound imaging system, the compression/scanning assembly adapted to compress the patient's breast chestwardly and scan the breast through said sheet with the motorized ultrasound transducer moving across the breast;

said sheet being taut at least in one direction when at rest but being partially conformable to locally deform when pressed against the patient's breast while the breast is being scanned therethrough with said motorized ultrasound transducer and said sheet is impregnated with an acoustic couplant; and said porous material being sufficiently sheer to view the compressed breast therethrough at least before said porous material is impregnated with said acoustic couplant;

said porous material including a spatially-uniform pore pattern that, when impregnated with said acoustic couplant during said scanning, promotes dissipation of air bubbles that might otherwise form between the breast and said scanning motorized ultrasound transducer, promoting locational stability of breast tissue being scanned, and flattening the breast when pressed against the breast with a selected force.

* * * * *